United States Patent
Zhao et al.

(10) Patent No.: US 10,308,764 B2
(45) Date of Patent: Jun. 4, 2019

(54) METHOD FOR PREPARING BIOBASED NYLON: POLYLACTAM

(71) Applicant: East China University of Science and Technology, Shanghai (CN)

(72) Inventors: Liming Zhao, Shanghai (CN); Jie Wei, Shanghai (CN); Jun Qian, Shanghai (CN); Juan Ma, Shanghai (CN); Xiaofeng Tang, Shanghai (CN); Yingyang Wu, Shanghai (CN); Yongjun Qiu, Shanghai (CN)

(73) Assignee: EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 21 days.

(21) Appl. No.: 15/542,602

(22) PCT Filed: Jul. 13, 2015

(86) PCT No.: PCT/CN2015/083914
§ 371 (c)(1),
(2) Date: Jul. 10, 2017

(87) PCT Pub. No.: WO2016/110079
PCT Pub. Date: Jul. 14, 2016

(65) Prior Publication Data
US 2018/0223043 A1    Aug. 9, 2018

(30) Foreign Application Priority Data

Jan. 8, 2015 (CN) .......................... 2015 1 0010169

(51) Int. Cl.
*C08G 69/16* (2006.01)
*C08G 69/24* (2006.01)
*C12P 13/00* (2006.01)

(52) U.S. Cl.
CPC .............. *C08G 69/16* (2013.01); *C08G 69/24* (2013.01); *C12P 13/005* (2013.01); *C12Y 401/01015* (2013.01)

(58) Field of Classification Search
None
See application file for complete search history.

(56) References Cited

U.S. PATENT DOCUMENTS 4,187,370 A    2/1980    Anshus et al.

FOREIGN PATENT DOCUMENTS

| CN | 101945997 | 1/2011 |
|---|---|---|
| CN | 101974151 | 2/2011 |
| CN | 104558589 | 4/2015 |
| JP | 2009159840 | 7/2009 |
| JP | 2011211993 | 10/2011 |
| JP | 2012214496 | 11/2012 |
| KR | 20090128767 | 12/2009 |
| KR | 20110123136 | 11/2011 |

OTHER PUBLICATIONS

International Search Report (Chinese and English) and Written Opinion of international application No. PCT/CN2015/083914, dated Sep. 23, 2015, 11 pages provided.

*Primary Examiner* — Samantha L Shterengarts
(74) *Attorney, Agent, or Firm* — Hamre, Schumann, Mueller & Larson, P.C.

(57) ABSTRACT

The invention relates to a preparation method of green nylon poly butyrolactams, the biological materials of GABA in vacuum under the condition of high temperature melt decomposition and purified butyrolactams, then by vacuum polymerization of green nylon poly butyrolactams. Compared with the prior art, the invention is prepared by biological method for the synthesis of a wide range of sources, to solve the problem of raw material supply PA4 for mass production, reduce the cost of reaction, and the reaction condition is simple, easy to implement simplified synthesis steps, from the laboratory to the transformation of industrial production.

10 Claims, 4 Drawing Sheets

METHOD FOR PREPARING BIOBASED NYLON: POLYLACTAM

BACKGROUND OF THE INVENTION

Technical Field

The present invention relates to a field for the synthesis of polymer materials, and more particularly to a process for producing green biobased nylon: polylactam using a biobased material γ-aminobutyric acid as a starting material.

Description of the Related Art

PA4, also known as polybutylactam, or polyamide 4, is a translucent or milky white thermoplastic resin, the relative density d=1.22~1.24, melting point 260~265° C. At room temperature dissolved in zinc chloride or other inorganic salt solution. It also can be dissolved in superheated water, and be hydrolyzed at 0.1 mol/dm3 (0.1 mol/L) sodium hydroxide, hydrochloric acid at 100° C. PA4 own better thermal stability than other nylon, which mainly used in synthetic fiber, artificial leather, and synthetic paper. PA4 artificial leather was flexible, porous, and no static electricity, which could be used into plastic products by injection molding or extrusion processing.

As PA4 has a similar hydrophilicity to cotton and silk, and can be used as a drawing fiber, film-forming agent and other molding compounds, its fiber product research has long been valued. PA4 is closer to natural fibers than other synthetic fibers. The moisture absorption curve of PA4 crosses the moisture absorption curve of cotton at 45% relative humidity. Under this humidity, the moisture absorption rate of cotton is higher than that of PA4, and the moisture absorption rate of PA4 is higher than that of cotton when humidity was higher than 45%. The moisture absorption performance of the two is close, thus PA4 can replace the cotton fiber to meet the relevant needs.

PA4 is a polymer obtained by anionic ring-opening polymerization of butyrolactam, and its structure is mainly composed of an amide bond and a methine group. The methylene group is a hydrophobic group. Polymers which have a number of methine groups more than 7 (nylon 610, 1010, and 12) is almost completely hydrophobic, and the amount of the amide bond is relatively reduced. Thus they could not fully form a complete fiber. Another example is the nylon 3, 2 polymers, although the hygroscopicity is excellent, but the processing performance is poor. Considering the moisture absorption and processing performance of the material, PA4 is the best choice in all nylon products.

Under normal circumstances, polyamide products, such as nylon 6 and nylon 66, is not degradable in the natural environment. However, PA4 has excellent biodegradability. Furthermore, the melting point of PA4 was about 260° C., which give PA4 good thermal and mechanical properties. The PA4 has excellent biodegradability and biocompatibility compared with other nylon materials, which has broad application prospects for tissue engineering for biomedical materials.

The general production process of PA4 is: butyrolactone ring-opening polymerization to produce linear polymer in the presence of catalyst. A process for the preparation of PA4 from alpha-pyrrolidone (butyrolactam) is disclosed in U.S. Pat. No. 4,187,370: the calculated purified 2-pyrrolidone is fed to a reactor equipped with a vacuum distillate inlet and then added 85.7% purified potassium hydroxide; the reactor was purged with nitrogen, and then 2-pyrrolidone was distilled under reduced pressure to remove the water produced by the reaction of pyrrolidone and potassium hydroxide. The reaction solution was cooled to 30° C. and passed under vacuum to a calculated carbon dioxide to the solution, and the reactor was brought to atmospheric pressure by the addition of nitrogen. The mixture was heated in the presence of stirring and maintained at 50° C. for 12 hours and then transferred to another vessel. In the case of stirring, 2% aqueous sulfuric acid was metered into the product reaction mixture until the pH 7. High molecular weight PA4 solid was obtained by centrifugation. The method belongs to the typical anionic ring-opening polymerization method.

The source of butyrolactam is still the key to PA4 industrial production. Butyrolactam is mainly produced by fossil-based chemical method at present. There were number of production processes: Taffet first used electrolysis in the production of 4-butyrolactam by succinimide amine in 1907. Due to power consumption, low product yield and unavailable raw materials and other reasons, Taffet method was unindustrialized. The Reppe method used acetylene and formaldehyde as raw materials, hydrogenation at high temperature and pressure to produce 1,4-butanediol, and dehydrogenation cyclization to produce 4-butyrolactone, and then ammonia reaction to produce butyrolactam. Reppe method is the first industrial butyrolactam production method. the United States General Aniline and film companies, Germany's BASF companies have used this route to produce 4-butyrolactam. The other method is Maleic anhydride method, which can be divided into one-step and two-step method. The United States Petrochemical Company used one-step Maleic anhydride method, with maleic anhydride and hydrogen, chlorine, heating step by step to get butyrolactam. Japan's Mitsubishi Chemical Corporation using two-step Maleic anhydride method: producing 4-butyrolactone by catalytic hydrogenation from maleic anhydride, and then ammoniated to produce 4-butyrolactam. Furthermore, methyl acrylate or ethyl ester and hydrocyanic acid reaction to be cyano-methylated or ethyl ester, and then hydrogenation to get butyrolactam. In addition, some studies reported the methods used crylonitrile or butadiene as raw materials can be prepared to produce butyrolactam. These methods all have to use non-renewable resources as raw materials, and under the high temperature and high pressure reaction to produce butyrolactam, which makes the high production cost of butyrolactam, resulting in high cost of PA4, greatly limiting the application of PA4.

Butyrolactone was not only used as the polymer monomer, but also as an important industrial solvent, pharmaceutical and chemical raw material. Butyrolactam worldwide annual consumption was about 15 million tons. The main producers are the United States General Aniline and Zizi Company (GAF) and Germany's BASF, Japan's Mitsubishi Chemical Company. There are only two manufacturers in china, and the annual output was less than 500 tons. The restriction of raw materials makes this excellent synthetic fiber (PA4) product has not yet industrial production in China.

Chinese Patent ZL201010522612.9 discloses a preparation method of bio-based nylon polybutyl lactam which comprises the following steps: converting the biomass raw material to glutamic acid by fermentation and then converting by glutamic acid decarboxylase, and then extraction and purification to obtain purified γ-aminobutyric acid. The bio-based nylon polybutyl lactam finally get by high-pressure polymerization. Compared with the prior art, the invention does not need ring-opening polymerization with butyrolactam as raw material, which solve the problem of raw material supply of PA4 production. Furthermore, the use of biotransformation process to replace high temperature and high pressure process greatly reduces the production cost, which makes the PA4 large-scale application possible. However, the method also excites the following problems: First, the high pressure polymerization of polybutyl lactam conditions was harsh, which is difficult to large-scale production in the industrialization. Second, the molecular weight of polybutyl lactam by one-step synthetic is low, which have yet to be improved.

BRIEF SUMMARY OF THE INVENTION

The object of the present invention is providing a process for the preparation of green nylon polybutyl lactam in order to overcome the drawbacks of the prior art described above.

The object of the present invention can be achieved by a method for producing a green nylon polybutyl lactam which is characterized in that the bio-base material γ-aminobutyric acid is melted and purified under reduced pressure and high temperature to obtain butyrolactam. Nylon polybutyl lactam was then obtained by reduced pressure polymerization.

The method comprises the following steps:

(1) high temperature melting: γ-aminobutyric acid was firstly stirred in a nitrogen atmosphere, and then full melted at 200-225° C. conditions, to obtain yellowish oily liquid butyrolactam with a small amount of water;

(2) vacuum purification: the yellowish oily liquid butyrolactam was placed in a vacuum oven 70° C. The purified yellowish oily liquid butyrolactam was obtained by water evaporation;

(3) Decompression polymerization: The catalyst was added to the purified butyrolactam, and the air in the reactor was removed by nitrogen. The mixture was heated to 50° C. by oil bath and then stirred continuously until the catalyst reacted completely with butyrolactam. The initiator was added under the above conditions to react for 8-15 h, the polymer is capped after adding formic acid, and the final reaction product is washed with water and acetone and then dried to obtain white solid product PA4.

The γ-aminobutyric acid is converted from biomass material by fermentation and then conversed by glutamic acid decarboxylase. The γ-aminobutyric acid can be prepared by the method disclosed in the patent ZL201010522612.9.

The entire reaction was carried out at a nitrogen rate of 3-5 ml/min.

The weight ratio of butyrolactam:catalyst:initiator was 1:(0.25-0.375):(0.5-0.75) during the reduced pressure polymerization process.

The catalyst is sodium, sodium hydroxide or potassium hydroxide.

The initiator is benzoyl chloride or sebacic acid chloride.

The polymer product may also be end-capping by addition of formic acid after the polymerization reaction.

The purity of the intermediate product butyrolactam obtained in step (2) is higher than 99.6%.

The molecular weight of final white solid PA4 product obtained in step (3) is higher than 10,000.

Compared with the prior art, the synthetic raw materials of this invention are synthesized by biological method, which have a wide range of sources. This method reduces the reaction cost, and the conditions of the whole reaction process are simple. The synthesis steps are simplified and it is easy to implement the large-scale production from the laboratory. The invention adopts γ-aminobutyric acid as raw material to produce the intermediate product of butyrolactam by high temperature melting method. Since γ-aminobutyric acid is lobular crystal (methanol-ether), needle-like crystal (water-ethanol) (Decomposed under rapid heating). The dissociation constant Ka and Kb of γ-aminobutyric was $3.7 \times 10^{-11}$ and $1.7 \times 10^{-10}$ at 25° C. respectively. γ-Aminobutyric is soluble in water, slightly soluble in hot ethanol, insoluble in other organic solvents. It will decompose into pyrrolidone and water above the melting point. Appearance: white crystalline or crystalline powder. The melting step could omit the treating the solvent and the catalyst steps. Compared with the patent ZL201010522612.9, the polymer obtained by this patent has higher molecular weight, and the synthesis conditions is easy to achieve. The purpose of vacuum purification is to avoid contact with oxygen in the air to obtain a higher purity butyrolactam. The catalyst is a cationic ring opening method to open the polymerization reaction.

DETAILED DESCRIPTION OF THE INVENTION

The invention will now be described in detail with reference to the accompanying figures and examples.

Embodiment 1

(1) high temperature melting: 80 g of γ-aminobutyric acid was added in 500 ml three-necked flask. The γ-aminobutyric acid as evenly spread evenly, close to the inner wall of the flask. A magnetic stirrer rotor was then thrown into three-necked flasks, which place in a magnetic stirring oil bath. Three-necked flasks were connected to nitrogen tanks, condensing equipment and thermometers, respectively, and adjusted to a nitrogen rate of 3 ml/min. First, the heating temperature was set at 190° C. to melt γ-aminobutyric acid. The temperature was raised to 190° C. and then incubated for 20 minutes. The temperature was raised 5° C. every 10 minutes until 225° C., and the mixture was incubated for 1 hour. After that, turn off the heating power, until mixture natural cooling. Place the resulting liquid in a glass instrument and store in a cool place.

Figure 1:
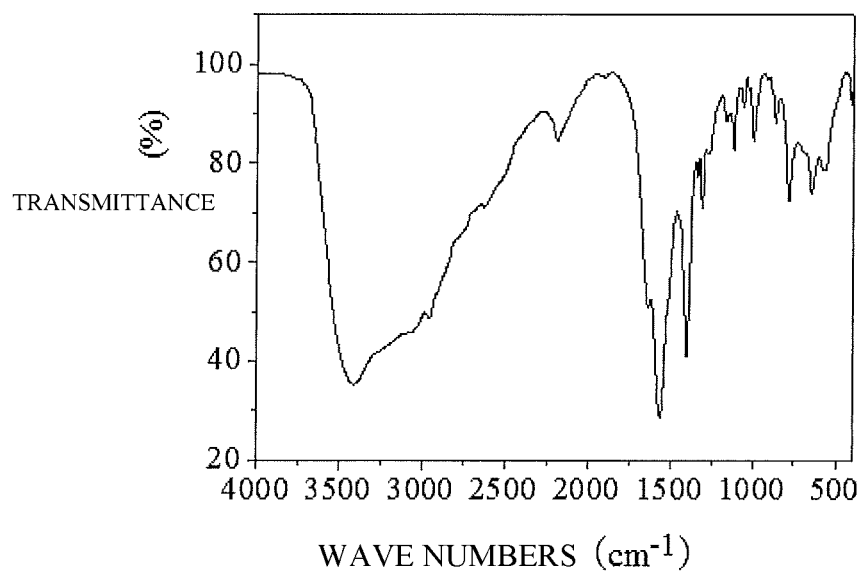
FIG. 1 shows the infrared spectrum of γ-aminobutyric acid.
Figure 2:
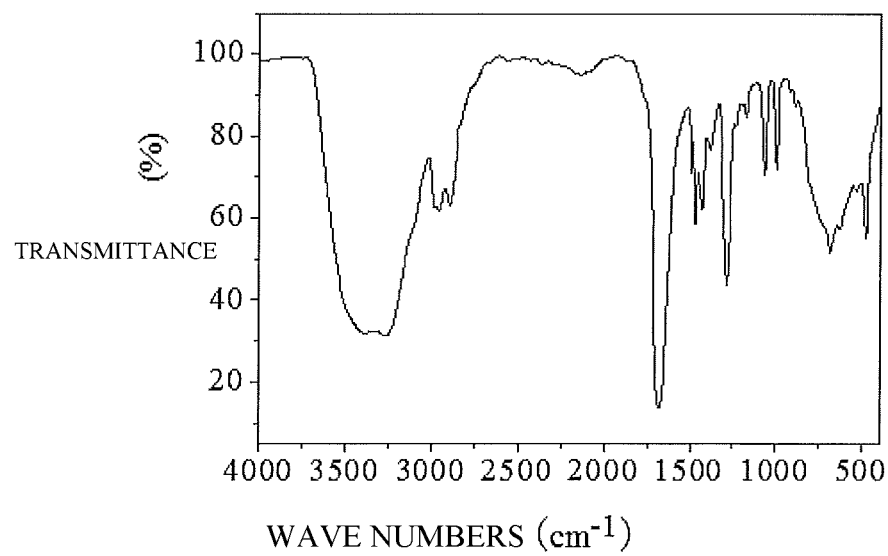
FIG. 2 is an infrared spectrum of butyrolactam obtained in Example 1.
Figure 3:
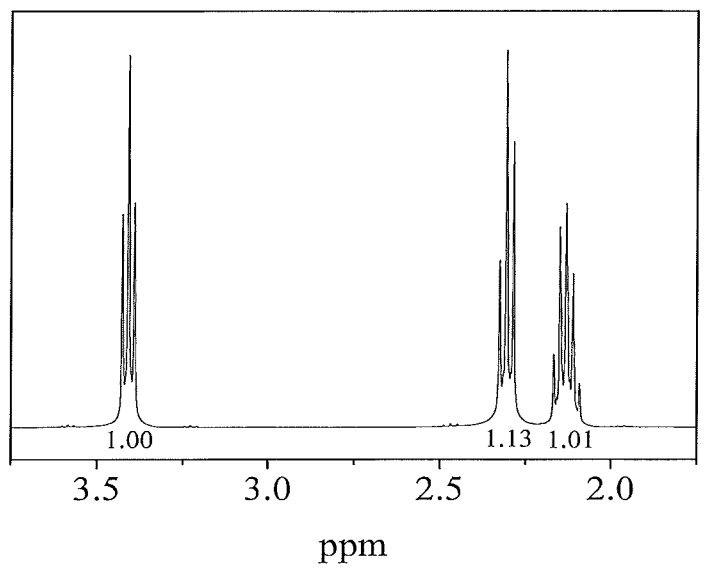
FIG. 3 is a nuclear magnetic resonance spectrum of butyrolactam obtained in Example 1.

(2) Vacuum purification: The prepared liquid was placed in a vacuum oven at 70° C. and the water was evaporated for 24 hours to obtain about 50 g purified yellowish oily liquid (butyrolactam). The infrared spectrum and the nuclear magnetic resonance spectrum of the prepared butyrolactam are shown in FIG. 2-3. Infrared spectrum showed three characteristic peaks (750 cm$^{-1}$, 1250 cm$^{-1}$ and 1500 cm$^{-1}$), which indicate that the material is γ-aminobutyric acid (FIG. 1). The characteristic peaks of 720 cm$^{-1}$, 1280 cm$^{-1}$ and 1600 cm$^{-1}$ in FIG. 2 indicated that the material is γ-butyrolactam; The characteristic peaks at 2.2, 2.35, and 3.4 indicate that the substance is γ-butyrolactam.

Decompression polymerization: 20 g butyrolactam and 5 g sodium were placed in 500 ml four-necked flask. A magnetic stirrer rotor was then thrown into four-necked flasks, which place in a magnetic stirring oil bath. Four bottlenecks were connected nitrogen tank, condensing equipment, constant pressure funnel and thermometer respectively, and then adjust the nitrogen rate of 3 ml/min. The mixture was reacted for 3 hour at 50° C. with stirring, and then added 10 g of benzoyl chloride. After the reaction was carried out for 8 hours in above condition, the polymer was capped by adding 120 ml formic acid. The product was then rinsed three times using the mixture of water and acetone (1:1; v:v), and the unreacted monomer was washed off. The final PA4 product was dried as a white solid product and weighed about 10 g.

Embodiment 2

(1) high temperature melting: 100 g of γ-aminobutyric acid was added in 500 ml three-necked flask. The γ-aminobutyric acid as evenly spread evenly, close to the inner wall of the flask. A magnetic stirrer rotor was then thrown into three-necked flasks, which place in a magnetic stirring oil bath. Three-necked flasks were connected to nitrogen tanks, condensing equipment and thermometers, respectively, and adjusted to a nitrogen rate of 5 ml/min. The heating temperature was set at 220° C. to melt γ-aminobutyric acid. The reaction was carried out for 2-3 hours until the water in the water pipe is no longer increased. Then turn off the heating power, until its natural cooling. Place the resulting liquid in a glass instrument and store in a cool place.

(2) Vacuum purification: The prepared liquid was placed in a vacuum oven at 70° C. and the water was evaporated for 36 hours to obtain about 65 g of the purified yellowish oily liquid (butyrolactam).

(3) Decompression polymerization: 30 g of butyrolactam and 7.5 g of potassium hydroxide were placed in a 500 ml three-necked flask. A magnetic stirrer rotor was then thrown into three-necked flasks, which place in a magnetic stirring oil bath. The three-necked flask was connected to a condensing apparatus, constant pressure funnel and vacuum distillation unit, and adjust the nitrogen rate of 5 ml/min. The oil bath temperature was set at 50° C., and after 5 h of stirring, 15 g of sebacic acid chloride was added. Keep the polymerization conditions unchanged, the reaction was carried out for 10 hours, and then turned off the heating power, until mixture natural cooling. The reaction product was washed three times using the mixture of water and acetone (1:1; v:v), and the unreacted monomer was washed off. The final PA4 product was dried as a white solid product and weighed about 15 g.

Figure 4:
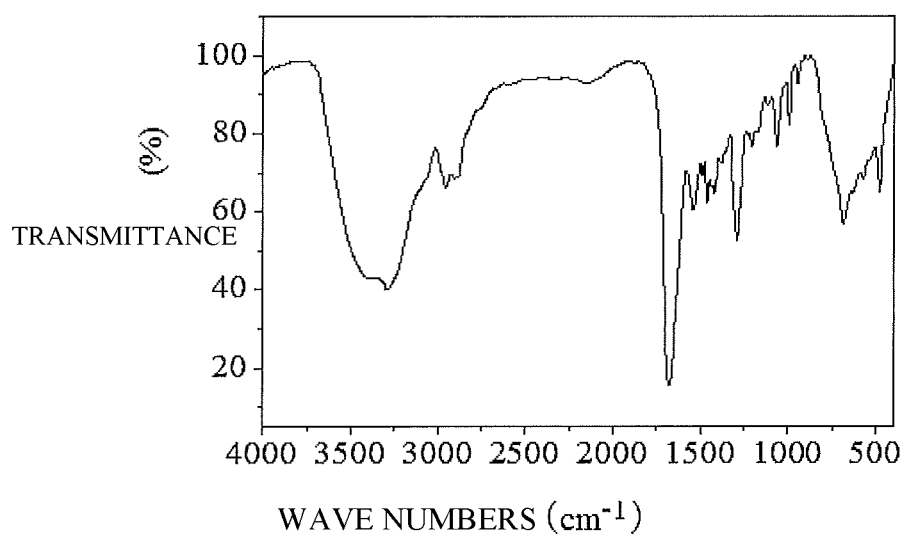
FIG. 4 is an infrared spectrum of PA4 obtained in Example 2.
Figure 5:
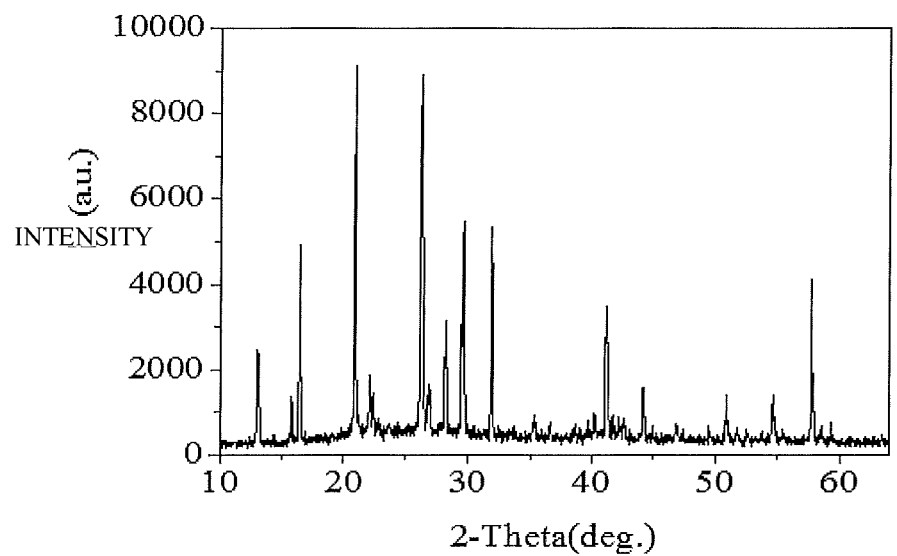
FIG. 5 is an X-ray diffraction pattern of PA4 obtained in Example 2.
Figure 6:
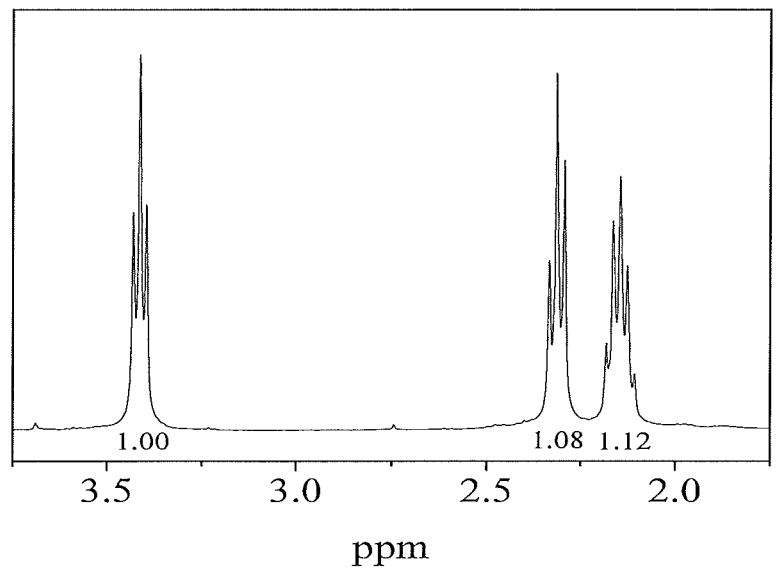
FIG. 6 is a nuclear magnetic resonance spectrum of PA4 obtained in Example 2.

PA4 solid (10 g) obtained by polymerization was subjected to two-step solid polycondensation under nitrogen atmosphere to increase the molecular weight. The molecular weight of PA4 was remarkably increased detecting by the viscosity method. The infrared spectrum, X-ray diffraction spectrum and nuclear magnetic resonance spectrum of the obtained PA4 are shown in FIG. 4-6. Some characteristic peaks was identified, such as the characteristic peaks at 730 cm$^{-1}$, 1000 cm$^{-1}$ and 1580 cm$^{-1}$ in FIG. 4; the characteristic peaks at 13, 17, 27, 29, 31, 42, 44, 52 in FIG. 3; the characteristic peaks at 2.2, 2.35, 3.4 in FIG. 6. The above results indicated that the substance is PA4.

Embodiment 3

Butyactam (30 g) obtained by vacuum purification process in Example 2 was placed in a 500-ml three-necked flask and added 10 g of potassium hydroxide. A magnetic stirrer rotor was then thrown into three-necked flasks, which place in a magnetic stirring oil bath at 50° C. The three-necked flask was connected to a condensing apparatus, constant pressure funnel and vacuum distillation unit, and adjust the nitrogen rate of 5 ml/min. The mixture was reacted with stirring until the potassium hydroxide and butyrolactam were consuming completely. Then add 22 g benzoyl chloride, and maintain the same polymerization conditions to react 15 h. Turn off the heating power, until mixture natural cooling. The reaction product was washed twice with a mixture of water and methanol in a volume ratio of 1:1 and then washed twice with a large amount of acetone, and the unreacted monomer was washed off. The final PA4 product was dried as a white solid product and weighed about 15 g.

Embodiment 4

(1) 5.2 g of γ-aminobutyric acid was dissolved in 250 ml of toluene, and then 15 g of Al2O3 was added. The whole reaction was carried out in a 500-ml three-necked flask and heated to 80° C. using an induction cooker for 8 h. After the completion of the reaction, the whole glass apparatus was cooled to room temperature. The catalyst was filtered, and the product obtained by filtration was washed with the toluene and chloroform mixture (1:1; v:v). The solvent was removed by rotary evaporation to obtain the yellow liquid oily butyrolactam.

(2) Decompression polymerization: 20 g of butyrolactam and 5 g of sodium were placed in a 500 ml four-necked flask. A magnetic stirrer rotor was then thrown into four-necked flasks, which place in a magnetic stirring oil bath. Four bottlenecks were connected nitrogen tank, condensing equipment, constant pressure funnel and thermometer respectively, and then adjust the nitrogen rate of 3 ml/min. The reaction was carried out for 6 h with stirring at 70° C. Then, 10 g of benzoyl chloride was added and keep the above polymerization conditions for 10 hours. Polymer was capped by adding 120 ml of formic acid. The reaction product was washed twice with a mixture of water and acetone in a volume ratio of 1:1, and the unreacted monomer was washed off. The final PA4 product was dried as a white solid product and weighed about 8 g.

Embodiment 5

Figure 7:
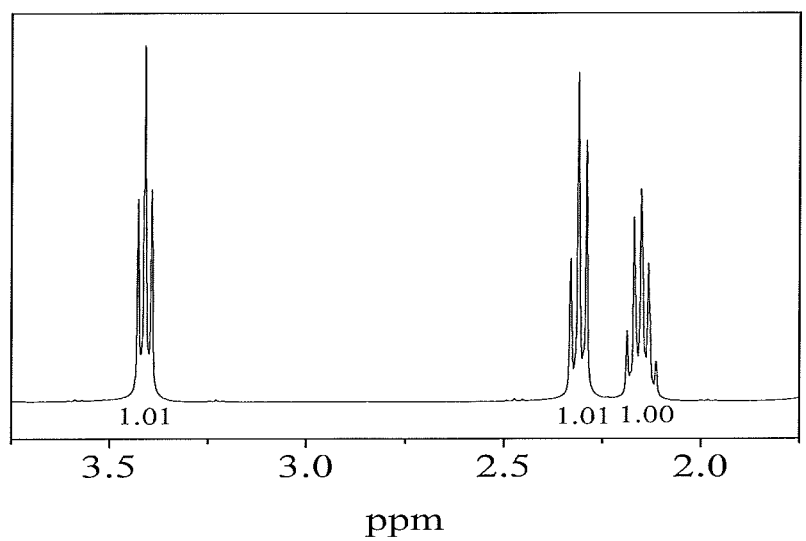
FIG. 7 is a nuclear magnetic resonance spectrum of PA4 obtained in Example 5.

Take 50 g of butyrolactam prepared by chemical process in a four-necked flask and added 13 g of sodium. A magnetic stirrer rotor was then thrown into four-necked flasks, which place in a magnetic stirring oil bath. Four bottlenecks were connected nitrogen tank, condensing equipment, constant pressure funnel and thermometer respectively, and then adjust the nitrogen rate of 4 ml/min. The reaction was carried out for 3 h with stirring at 50° C. Then, 26 g of benzoyl chloride was added and dissolved it in tetrahydrofuran. Keep the above polymerization conditions for 15 hours, and the polymer was capped by adding 120 ml of formic acid. The reaction product was washed three times with a mixture of water and acetone in a volume ratio of 1:1, and the unreacted monomer was washed off. The final PA4 product was dried as a white solid product and weighed about 28 g. The NMR spectrum of the obtained PA4 is shown in FIG. 7. The characteristic peaks of 2.2, 2.35, and 3.4 at FIG. 7 indicated that the product is PA4.

The invention claimed is:

1. A method for preparing a green nylon polybutyrolactam, comprising:
    obtaining a purified butyrolactam from processes including melting γ-aminobutyric acid and vacuum purification of butyrolactam; and
    obtaining a green nylon polybutyrolactam from a process including vacuum polymerization of the purified butyrolactam.

2. The method according to claim 1,
    wherein the process of melting γ-aminobutyric acid includes stirring the γ-aminobutyric acid under nitrogen atmosphere and melting γ-aminobutyric acid at a temperature of 200-225° C. to obtain an oily liquid containing a small amount of water;
    the process of vacuum purification includes vacuum drying the oily liquid in a vacuum chamber at a temperature of 70° C.;
    the process of vacuum polymerization includes:
        adding a catalyst to the purified butyrolactam in a reactor and flowing nitrogen to remove air in the reactor,
        heating the purified butyrolactam in an oil bath to a temperature of 50° C., and stirring until the catalyst reacts with the purified butyrolactam,
        adding an initiator and reacting for 8-15 hours to obtain a reaction product,
        washing the reaction product with water and acetone, and
        drying the reaction product to obtain green nylon polybutyrolactam.

3. The method according to claim 2, wherein γ-aminobutyric acid is obtained from a process including fermenting a biomass, conducting enzymatic conversion with glutamic acid decarboxylase, and performing extraction and purification.

4. The method according to claim 2, wherein the method is conducted under a nitrogen atmosphere with a nitrogen flow rate of 3-5 ml/min.

5. The method according to claim 2, wherein a mass ratio of the butyrolactam, the catalyst, and the initiator in the process of vacuum polymerization is 1:(0.25-0.375):(0.5-0.75).

6. The method according to claim 2, wherein the catalyst includes sodium, sodium hydroxide, or potassium hydroxide.

7. The method according to claim 2, wherein the initiator includes benzoyl chloride or sebacoyl chloride.

8. The method according to claim 1, further comprising adding formic acid to cap a termini of the green nylon polybutyrolactam.

9. The method according to claim 2, wherein the purified butyrolactam has a purity of higher than 99.6%.

10. The method according to claim 2, wherein the green nylon polybutyrolactam has a molecular weight of 10,000.

* * * * *